United States Patent [19]

Eagles et al.

[11] Patent Number: 5,840,777
[45] Date of Patent: Nov. 24, 1998

[54] METHOD OF PRODUCING POLYSACCHARIDE FOAMS

[75] Inventors: Dana Burton Eagles, Sherborn; George Bakis, West Roxbury; Andrew Bruce Jeffery, North Quincy; Constantinos Mermingis, Boston, all of Mass.; Thomas Henry Hagoort, Montclair, N.J.

[73] Assignee: Albany International Corp., Albany, N.Y.

[21] Appl. No.: 196,079

[22] PCT Filed: Jun. 18, 1993

[86] PCT No.: PCT/US93/05993

§ 371 Date: Feb. 15, 1994

§ 102(e) Date: Feb. 15, 1994

[87] PCT Pub. No.: WO94/00512

PCT Pub. Date: Jan. 6, 1994

[30] Foreign Application Priority Data

Nov. 19, 1992 [GB] United Kingdom .................. 9224255
Jun. 19, 1993 [GB] United Kingdom .................. 9212976

[51] Int. Cl.⁶ .................. C08J 9/00; C08J 9/02; C08J 9/06
[52] U.S. Cl. .................. 521/82; 521/84.1; 521/92; 521/134; 521/138; 521/140
[58] Field of Search .................. 536/3; 521/82, 521/84.1, 92, 134, 138, 140

[56] References Cited

U.S. PATENT DOCUMENTS

| | | |
|---|---|---|
| 3,598,742 | 8/1971 | Jamison et al. . |
| 3,653,383 | 4/1972 | Wise . |
| 3,688,437 | 9/1972 | Hamrin . |
| 3,868,355 | 2/1975 | Rodgers . |
| 3,992,333 | 11/1976 | Emmons et al. ..................... 521/89 |
| 4,002,178 | 1/1977 | Fiore et al. . |
| 4,139,699 | 2/1979 | Hernandz et al. . |
| 4,292,972 | 10/1981 | Pawelchak et al. ..................... 128/296 |
| 4,421,583 | 12/1983 | Aldred et al. . |
| 4,547,529 | 10/1985 | Lee et al. ..................... 521/122 |
| 4,562,110 | 12/1985 | Tong . |
| 4,613,497 | 9/1986 | Chavkin . |
| 4,642,903 | 2/1987 | Davies . |
| 4,663,159 | 5/1987 | Brode, II et al. . |
| 4,793,337 | 12/1988 | Freeman et al. . |
| 4,948,575 | 8/1990 | Cole et al. . |
| 5,057,606 | 10/1991 | Garbe . |
| 5,089,606 | 2/1992 | Cole et al. ..................... 536/54 |
| 5,156,765 | 10/1992 | Smrt et al. ..................... 252/307 |
| 5,197,945 | 3/1993 | Cole et al. . |

FOREIGN PATENT DOCUMENTS

| | | |
|---|---|---|
| 62-81432 | 4/1987 | Japan . |
| 62-167331 | 7/1987 | Japan . |
| 653341 | 5/1951 | United Kingdom . |
| 1231506 | 5/1971 | United Kingdom . |
| 1283399 | 7/1972 | United Kingdom . |
| 1394741 | 5/1975 | United Kingdom . |
| 1394742 | 5/1975 | United Kingdom . |
| 1570485 | 7/1980 | United Kingdom . |
| 2103993 | 3/1983 | United Kingdom . |
| WO91/07951 | 6/1991 | WIPO . |

OTHER PUBLICATIONS

English language translation for JPA 62–167331.
English language translation for JPA 62–81432.
Blaine, George, Major R.A.M.C. "Experimental Observation on Absorbable Alginate Products in Surgery" Annals of Surgery, vol. 125, No. 1, Jan. 1947, pp. 102–114.
International Search Report dated Oct. 4, 1993.

*Primary Examiner*—Jeffrey Mullis
*Attorney, Agent, or Firm*—Kane, Dalsimer, Sullivan, Kurucz, Levy, Eisele and Richard

[57] ABSTRACT

A method of producing a polysaccharide foam is provided. The method comprises mechanically foaming an aqueous solution of a soluble polysaccharide and thereafter reacting the foam to produce stable foam. Typically, the soluble polysaccharide is an alginate, hyaluronate, carrageenans, chitosan or starch.

24 Claims, 3 Drawing Sheets

METHOD OF PRODUCING POLYSACCHARIDE FOAMS

DESCRIPTION

The present invention relates to a method of producing polysaccharide foams; in particular alginate, chitosan, starch and hyaluronate foams. The invention also embraces polysaccharide foamed materials produced in accordance with the method of the invention and wound dressings, foamed cell culture replicating media, barrier media for preventing tissue adherence and other absorbent materials comprising such foams.

Alginates, particularly calcium alginates and converted calcium alginates, have long been known for their ability to form fibres and yarns which can be knitted into fabrics or formed into nonwoven materials primarily for use as swabs or dressings for medical, surgical or other purposes.

For instance, British Patent Specification No. 1283399 describes and claims a method of preparing a soublized calcium-containing alginate material which comprises acidifying calcium alginate with a calculated quantity of acid sufficient to remove a desired amount of calcium, reacting the acidified calcium alginate with an excess of base selected from ammonia, amines and substituted amines and washing the solubilized calcium-containing alginate to remove the excess of base.

This material may be formed into a number of pieces of gauze which can then be further treated as described in the specification.

British Patent Specification No. 1394742 relates to a surgical dressing material comprising a layer of knitted gauze adhered to a layer of fibrous backing material, the gauze comprising alginate material and the dressing material being of lower flexibility and stretchability than the gauze itself.

British Patent Specification No. 1570485 relates to an absorbent material for aqueous fluids which comprises an open cell foam containing within the cells a hydrophilic gel having specific properties. Typical of the hydrophilic gels is alginates. The specification describes the incorporation of these materials in a reticulated foam; the gel being contained within the cells of the foam thus providing an absorbent material.

U.S. Pat. No. 4,421,583 relates to a non-woven alginate fabric useful as a wound dressing made by spreading a tow of calcium alginate filaments into a flow of water, overfeeding the spread filaments onto a water pervious support so that the filaments cross over each other, and drying the filaments so that they become bonded to each other at their points of contact where they cross over. The filaments used have preferably been pre-stretched in an atmosphere of steam and wash water and not dried and are preferably subsequently dried by suction on the water pervious support.

U.S. Pat. No. 4,793,337 discloses an improved adhesive structure for adhesion of an article to a fluid emitting wound, the structure having an absorbent region comprising an absorbent fibrous fabric or foam material intermediate first and second contact regions, whereby enhanced cohesion between the first and second regions and between the second region and the article under conditions of heavy fluid emission is provided. This specification discloses the use of sodium alginate in combination with a calcium powder by way of absorbent material.

U.S. Pat. No. 4,948,575 discloses a dimensionally stable alginate hydrogel foam wound dressing that absorbs wound exudate without any appreciable swelling. The wound dressing includes alkaline metal earth (except magnesium) salts and Group III metal salts of alginic acid. The hydrogel foam may be formed by mixing together a first liquid component comprising (a) an aqueous suspension of particles of a water insoluble di- or trivalent metal salt and (b) an effervescent compound which effervesces upon reaction with an acid; and a second liquid component comprising an aqueous solution of biocompatible, water-soluble acid wherein at least one of the components further comprises a water-soluble alginate dissolved therein. Upon mixing, the water-insoluble metal salt reacts with the water soluble acid to form a water soluble metal salt that is subsequently ionized. The polyvalent cations released from the water-soluble metal salt complex with the carboxylate groups of the water-soluble alginate causing the formation and precipitation of a water insoluble alginate hydrogel. At the same time the effervescent compound is reacting with the water soluble acid; the resultant evolution of gases effects the formation of a stable hydrogel foam.

Commercially available alginate products are marketed inter alia as haemostatic wound dressings using non-woven fibre technology. However non-woven alginate materials, while performing their function satisfactorily, are difficult to handle. Several attempts have been made to improve handling, for example Swedish Patent Application published under No. 424956 describes an alginate hydrogel wound dressing formed on a wound in combination with an elastic rubber-like composition. In another attempt at providing a more readily usable material, it has been proposed to use a freeze-dried foam as disclosed in U.S. Pat. No. 4,642,903. The disadvantage of all these prior art foam methods is that there is little or no control over the foam size and that the resultant products are relatively difficult to handle.

According to one aspect of the present invention, therefore, there is provided a method of forming a polysaccharide foam which comprises preparing an aqueous solution including a soluble polysaccharide and thereafter mechanically foaming the solution.

The foam may be produced by beating or otherwise mechanically agitating the material to cause the polysaccharide to foam. The mechanical foaming may involve the introduction of gas into the solution, and shearing of the solution to create a mixing effect which may result in a very fine dispersion of gas bubbles in the solution. In the early stages of mechanical foaming, when the total amount of gas entrained in the solution is small, the gas bubbles may be substantially spherical in shape. As the total volume of gas entrained in the solution increases, the gas bubbles may undergo a transition from the spherical shape to a substantially polyhedral shape, with the solution distributed in thin membranes between adjacent gas bubbles and in ribs or spokes where several gas bubbles come into very close proximity to each other; the result is a foamed polymer having gas dispersed throughout the solution in a cellular structure. It will be appreciated by a person skilled in the art that, in some embodiments of the present invention, the relative violence and/or period of agitation of mechanical action may be used to provide control over the foam pore size. The foam pore size may be controlled in the range 5–500$\mu$; typically 50–500$\mu$.

Said soluble polysaccharide may be alginic acid or hyaluronic acid. In some embodiments, said soluble polysaccharide may be a soluble polysaccharide salt such, for example, as an alginate or hyaluronate; typically, sodium alginate or sodium hyaluronate may be used. Alternatively, the soluble polysaccharide may be carrageenans, chitosan, starch, or separately, amylose or amylopectin. A person skilled in the art will appreciate that chitosan is soluble in acid, but is insoluble in neutral and basic solutions; on the other hand, starch is soluble in basic solutions. Thus, where chitosan is used in accordance with the present invention, the mechanical foaming step should be conducted in an acidic aqueous solution; where starch is used, foaming should be conducted in aqueous base.

In one aspect of the invention, a foaming agent may be included in the aqueous solution to assist in foaming the solution. The foaming agent may be a surfactant, typically an ionic or non-ionic surfactant. The ionic surfactant may be selected from sodium stearate, sodium dodecyl sulfate, alpha olefin sulfonates (commercially available under the trade name "Siponate 301-10"), sulfoalkyl amide, monocarboxyl coco imidazoline compounds, dicarboxyl coco imidazoline compounds and sulfated fatty polyoxyethylene quatenary nitrogen compounds.

Said non-ionic surfactant may be selected from octylphenol ethoxylate (commercially available from Rohm & Haas under the trade name TRITON X-100), modified linear aliphatic polyethers and sorbitan esters.

In another aspect of the invention, a plasticizer may be included in the aqueous solution. Said plasticizer may be selected from glycerol, glucose, polyhydric alcohols, triethanolamine and stearates.

In some embodiments, an oligomeric or polymeric foam modifier may be included in the aqueous solution; said foam modifier may be selected from polyethylene glycol, guar gum, albumin, gelatin, carboxymethyl cellulose, hydroxyethyl cellulose, hydroxypropyl cellulose, polyacrylamide, polyacrylic acid, polyvinyl alcohol, polyvinyl pyrrolidone, polyoxazoline and polyethyeneimine. These foam modifiers may be used to improve the flexibility and toughness of the polysaccharide foam.

In a particular aspect of the invention the foam modifier may be polyethylene glycol functionalised with vinyl groups such, for example, as acrylates. After foaming, the functionalised polyethylene glycol may be polymerised by irradiation (e.g. u.v. or electron) to form a polymer network within the foam; said network may improve the flexibility and toughness of the foam.

In a different aspect of the invention, the aqueous solution of polysaccharide may include a foam stabiliser. Said foam stabliser may be selected from ammonium stearate, dodecyl alcohol, tetradecanol, hexadecanol, tridecyloxypolyethanol and polyoxyethylated oleylamine.

In some embodiments, the resultant polysaccharide foam, including foam stabilizer, may be air dried after formation. On drying, the foam material in an interior region of the foam may "collapse" giving the appearance of crushed foam; the cells constituting the foam may distort such that in one dimension each cell may become smaller than in another dimension substantially normal to the one dimension; this change in shape can be described as a sphere distorting to an ellipsoid. When the cells distort in this way, the foam is referred to herein as a "collapsed" foam. The foam material juxtaposed the surface of the foam may maintain its integrity preserving its mean pore size and pore size distribution.

Where the polysaccharide is chitosan which is foamed in an acidic aqueous solution it may be desirable, in some embodiments, to remove the acid after foaming while the foam is still wet since, on drying, any acid present may have an injurious effect on the chitosan foam. Said acid may be removed after foaming by volatilisation or neutralisation. Typically, the acid may be aqueous acetic acid which may be removed by volatilsation.

In another aspect of the invention, the foam may be stabilized by cross-linking or coagulation thereby to provide a dimensionally stable foam. Typically, the foam may be cross-linked or coagulated while wet; where a foam stabilizer is used the foam may be cross-linked or coagulated after initial drying, the foam may then be re-dried.

When the polysaccharide is selected from alginic acid, alginate, hyaluronic acid, hyaluonate, and other soluble polysaccharide materials containing exchangeable counter-cations, the cross-linking may be effected by reacting the foamed polysaccharide with di- or tri- valent cations. Said polysaccharide foam may, in some embodiments, be immersed in or sprayed with a solution of the di- or tri-valent cations. Typically, the cations may be selected from $Ca^{2+}(aq)$, $Fe^{2+}(aq)$ and $Fe^{3+}(aq)$.

Alternatively, in some embodiments, an insoluble carbonate or hydrogen carbonate salt having one or more di- or tri-valent cations may be homogeneously dispersed in the foamed polysaccharide, and the foam may be subsequently treated with a strong acid to liberate carbon dioxide as gas and said cations which then cross-link with the polysaccharide to form a dimensionally stable foam structure. The strong acid may have a concentration of up to 1N, typically 0.1–0.2N. Typically, calcium carbonate may be used as an insoluble carbonate salt. This latter method of cross-linking has the advantage that a relatively thick foam may be stabilized uniformly through its thickness; typically a foam thickness of up to about 5 mm may be homogeneously stabilized using this method to provide a stable foam structure.

In a different aspect of the invention, the cross-linked alginate or hyaluronate foam may be "converted" by treatment with an aqueous solution of a reagent having solubilising mono-valent cations so that a proportion of the cross-linking di- or tri-valent cations in the foam may be replaced by the mono-valent cations, thereby imparting a degree of solubility in the foam; when contacted with water, the converted foam may form a gel. In some embodiments, the degree of conversion may be controlled; typically a small proportion of the cross linking cations may be replaced to provide a lightly gelling foam (when contacted with water). Alternatively, in some embodiments, substantially all the cross-linking cations may be replaced to provide a substantially water soluble foam. The reagent may be selected from sodium acetate and dilute hydrochloric acid. Typically, the treatment may be performed at a pH in the range 4–7.

Where the soluble polysaccharide is chitosan, the foam may be coagulated by treatment with base. Typically, said base may be sodium hydroxide solution. Alternatively, the chitosan foam may be cross-linked by ionic or covalent bonding. Ionic cross-linking may be obtained by treatment with an aqueous solution of polyvalent anions; typically one or more of sodium sulfate, octyl sulfate, lauryl sulfate, hexadecylsulfate, tripolyphosphate, pyrophospate and octapolyphosphate may be used as a source of polyvalent anions. In other embodiments, covalent cross-linking may be obtained by treating the chitosan foam with one or more dialdehydes e.g. glyoxal, glutaraldehye and dialdehyde starch.

Where the polysaccharide is starch, the starch foam may be coagulated by treatment with aqueous ammonium sulfate. Alternatively starch foam may be cross-linked by treatment with formaldehyde; this treatment may be performed in the gaseous or liquid state. If the treatment is performed in the liquid state a solution in alcohol may typically be employed.

The cross-linked or coagulated polysaccharide foam may be dried in air. After drying, the dry, cross-linked or coagulated foam may be washed with water and then redried. Washing may be used to remove e.g. any foaming agent or foam stabiliser residual in the foam.

Said aqueous solution of polysaccharide may further comprise one or more ingredients selected from particulate fillers, barium sulfate, pulp-like fibres of cellulose or other fibrous material and moisture retaining or reinforcing filler materials. Where barium sulfate is used, it will be appreciated that the resultant foam may be substantially opaque to X-rays; the foam may therefore be useful as a medical implant in radiography.

In some embodiments, the foam may be bleached. Bleach may be included in the aqueous solution of polysaccharide; typically, the bleach may be selected from hydrogen peroxide and sodium hypochlorite.

The present invention also includes a polysaccharade foam produced in accordance with the method of the invention; the foam can be controlled at various thicknesses, pore sizes and pore size distributions. The foam may be cross-linked or coagulated; the foam may be a soluble foam, an insoluble foam or a "converted" foam having a desired degree of solubility in at least part of the foam. Typically the foam may be an alginate, hyaluronate, chitosan or starch foam.

In another aspect of the invention, the foam, when wet, may be cast as a layer or as a shaped article. Said foam may be cast inter alia in the form of buttons, beads, balls, cylinders or hemispheres. In some embodiments, the foam may be cast in the shape of a part of a human or animal body e.g. in the shape of an ear or nose.

In a particular aspect of the invention, the foam may be cast as a layer on a substrate. Said substrate may be a woven or non-woven fibrous article, a film or a foam. In some embodiments, the substrate may comprise an assemblage of polysaccharide fibres or yarns. In a particular aspect of the invention the substrate may comprise another layer of polysaccharide foam in accordance with the invention. Said other layer foam may have a different mean pore size and/or pore size distribution from the first mentioned foam.

The foam may be cast as a thin foam layer having a thickness up to about 1 mm. Alternatively, the foam in accordance with the present invention may be cast as a thick foam layer having a thickness of up to about 50 mm. Said thick foam layer may have an interior layer of "collapsed" foam; the foam juxtaposed the surface of the foam may be not significantly collapsed, being similar in appearance and having a pore size and pore size distribution about equal to the foam when freshly formed.

The present invention also includes a wound dressing comprising a polysaccharide foam produced by the method in accordance with the present invention. Typically the wound dressing may comprise a layer of said polysaccharide foam. In some embodiments the foam may be disposed on a substrate, the substrate may be a polysaccharide fabric or composed of polysaccharide yarn.

The present invention also includes a cell culture replicating medium comprising a polysaccharide foam produced in accordance with the present invention; the cells to be replicated can be disposed in the pores in the foam to locate the cells.

In some embodiments, the cell culture replicating medium may constitute an implant, typically a bio-absorbable implant.

Cultured cells, e.g. mammalizing cells, may be disposed in the pores of the implant which may then be implanted surgically in a human or animal body. The implant containing cultured cells may encourage tissue growth in and around the implant in vivo.

The present invention also includes a barrier medium for preventing tissue adherence, said barrier medium comprising a polysaccharide foam in accordance with the invention.

In another aspect of the present invention, the polysaccharide foam may constitute a carrier for a beneficial agent formulation. Said beneficial agent formulation may be accommodated within the cells of the foam. Typically the formulation may comprise a beneficial agent and a pharmaceutically acceptable excipient therefor. In some embodiments, the beneficial agent may be a drug which can be administered to a patient transdermally. Typically, the beneficial agent formulation may be included in the aqueous solution of polysaccharide prior to foaming. Alternatively, however, the beneficial agent formulation may be incorporated in the foam after formation; in some embodiments the foam may be immersed in or sprayed with the formulation (which may itself be in solution); in other embodiments the formulation may be dispersed in a solid particulate form in the cellular structure of the foam, or produced by living cells (e.g. microbes) in the foam structure.

In yet another aspect of the present invention, a foam in accordance with the present invention, when wet, may be stored under pressure; typically the wet foam may be stored in a pressurised dispenser such, for example, as a conventional pressurised spray can. In some embodiments, the wet foam may be incorporated with a propellant to assist in subsequent delivery of the foam from the dispenser; said propellant may be any suitable propellant known to a person skilled in the art e.g. a gaseous lower alkane (propane, butane, pentane and the like), nitrogen and carbon dioxide. It will be appreciated that storage under pressure constitutes a convenient method of storing a wet foam prior to use; when required, the foam may simply be dispensed directly to the environment of use.

For example, a wet foamed wound dressing in accordance with the invention may be stored under pressure in a dispenser and dispensed directly onto a patient's skin to treat e.g. abraded skin, burns and open wounds. A wet foam carrying a beneficial agent in accordance with the present invention may be stored and dispensed in the same way to provide rapid therapeutic treatment of a wound or other injury when required. It will be appreciated by a person skilled in the art that a foamed wound dressing or beneficial agent formulation carrier which is stored in a pressurised dispenser may be particularly suitable for the purposes of applying first aid to a patient in an emergency.

Following is a description by way of example only and with reference to the accompanying drawings of methods of carrying the invention into effect.

EXAMPLE 1

Figure 1:
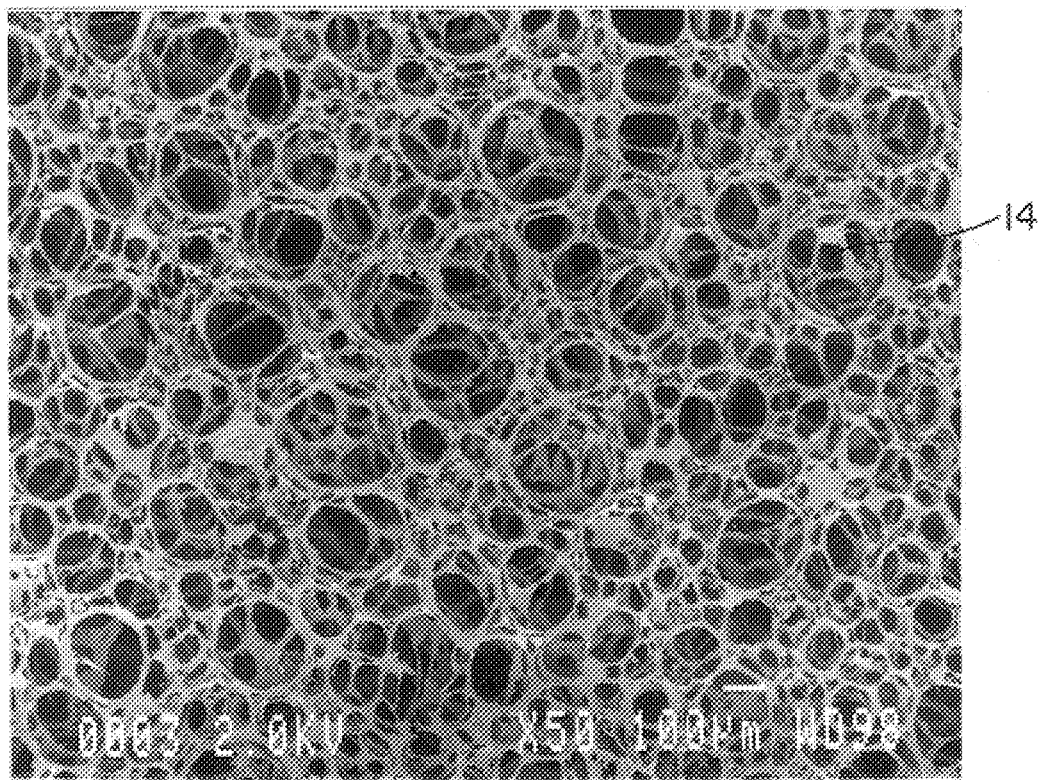
FIG. 1 is a scanning electron microscope ("SEM") photograph showing a surface of a single layer foam produced in accordance with the present invention.

A solution containing 3 wt % of sodium alginate having a viscosity of 1500 centipoise was prepared and to 100 grams of this solution was added 0.1 grams of sodium dodecyl sulfate as a foaming agent. The resultant solution was beaten with a Kitchenaid mixer to form a foam. The foam was spread on a metal tray and cross-linked with an aqueous solution containing 5% by weight calcium chloride. The foam was then dried and after drying was found to be 0.05 mm thick and weighing 7 grams per square meter. A scanning electron microscope photograph of the cross-linked foam revealed an open pore structure which was found to have an air permeability of 110 m/min measured at 12.7 mm $H_2O$ pressure.

A portion of the foam produced in the manner described above was converted by placing it in an aqueous solution of hydrogen chloride with a pH of 5 for 30 minutes. The conversion did not affect the gauge weight or pore size, but did change the solubility characteristics. Contact of the non-converted foam with a 1% sodium citrate solution did not affect the structure, whereas the contact of the converted foam with the same 1% sodium citrate solution resulted in a gelation of the foam. This latter action suggested the solubility characteristics were modified by the conversion process.

EXAMPLE 2

A 3"×3" gauze pad comprising a 12-ply 20×12 mesh fabric was used as a substrate for a layer of alginate foam as described in Example 1. The foam was spread on the fabric and cross-linked with a 5% aqueous solution of calcium chloride. The material was then dried and it was found that the cross-linked foam had adhered to the gauze pad to form a coating. A photomicrograph of the resultant structure reveals a thin, 0.05 mm thick foam coating on the gauze pad which had a similar structure as the foam without the substrate described in Example 1.

When the coated pad was placed in an aqueous solution of hydrogen chloride at a pH of 5 for 30 minutes, the calcium structure was converted to a soluble form. Contact of the converted material with sodium citrate once again resulted in gelation of the alginate coating.

EXAMPLE 3

An aqueous solution containing 2 wt % sodium alginate was prepared. To this solution was added 0.2 wt % ammonium stearate as a foam stabiliser and 2 wt % calcium carbonate. The mixture was then well mixed in a kitchenaid mixer to produce a foam having the calcium carbonate dispersed therethrough. The foam was drawn in a plastic tray, and 200 ml of 0.1N hydrochloric acid was then added in the tray. As a result of the addition of strong acid, the foam cross-linked. After drying, the foam was found to have a final thickness of 2.1 mm, a density of 0.22 g/cm³ and an air permeability of 6 m/min at a pressure of 12.7 mm $H_2O$.

The foam was found to be coagulated uniformly through its thickness.

EXAMPLE 4

A 3% wt aqueous solution of sodium alginate was prepared. To the solution was added 0.85 grams of sodium dodecyl sulphate per 100 grams of alginate solution as a foaming agent. In addition, 2.3 grams of ammonium stearate per 100 grams of alginate solution was added as a foam stabilizer. The resultant solution was beaten with a Kitchenaid mixer to form a foam. The foam was spread on a polyester sheet and allowed to air dry. The surface of the dried foam maintained a similar appearance to the wet foam and did not collapse; the foam material in the interior of the foam was found to have "collapsed" and had the appearance of crushed foam. The dried foam was immersed in a 5% wt calcium chloride solution and then allowed to air dry. Once again the dried foam maintained the appearance of the original drawn material. Inspection under an optical microscope revealed the foam was an open-cell structure with fairly uniform pore sizes. The foam had a final thickness of 2.8 mm, a density of 0.05 g/cm, and a permeability of 90 m/min at 12.7 mm $H_2O$.

EXAMPLE 5

To a solution of similar composition to Example 1 was added 1 gram of anhydrous glycerol per gram of alginate material. The solution was foamed mechanically, drawn into a desired thickness and allowed to air dry. The dried foam was cross-linked using a 5% wt calcium chloride solution and air dried. The resultant foam had a final thickness of 0.25 mm, a density of 0.14 g/cm³ and an air permeability of 100 m/min at 12.7 mm $H_2O$ pressure. After 3 months under ambient conditions, the foam had a similar handling ability as a newly formed foam.

EXAMPLE 6

Figure 2:
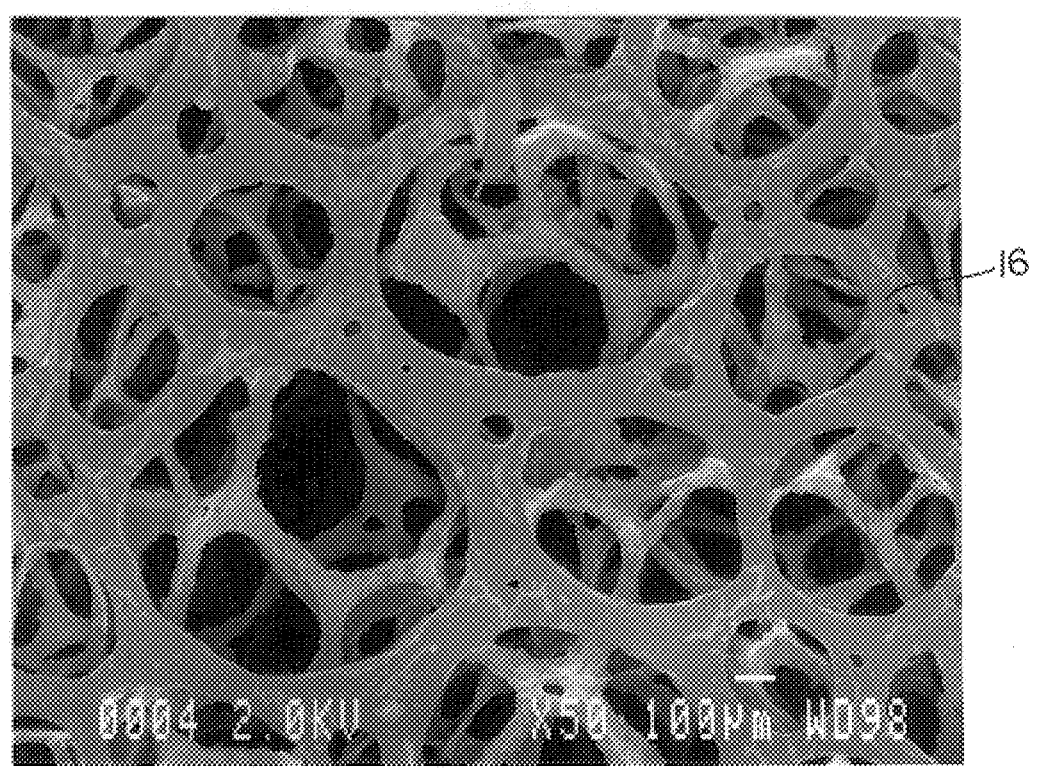
FIG. 2 is an SEM photograph of another surface of the single layer foam of FIG. 1.
Figure 3:
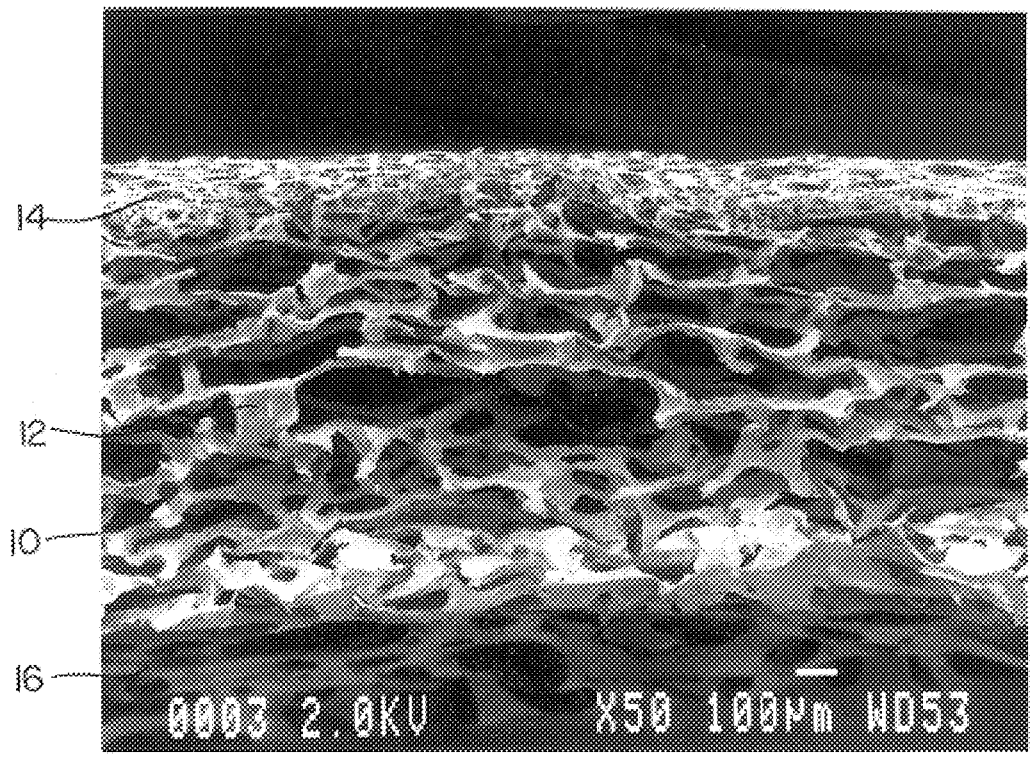
FIG. 3 is an SEM photograph of a cross section through the thickness of the single layer foam of FIGS. 1 and 2.

A single layer alginate foam was produced by a method similar to the method described in Example 4 above. FIGS. 1 to 3 are Scanning Electron Microscope photographs of the resultant dried foam (10). It will be noted that an interior region (12) of the foam is "collapsed" giving the appearance of "crushed" foam, while the surfaces (14, 16) of the foam substantially maintain their pore size and pore size distributions.

EXAMPLE 7

Figure 4:
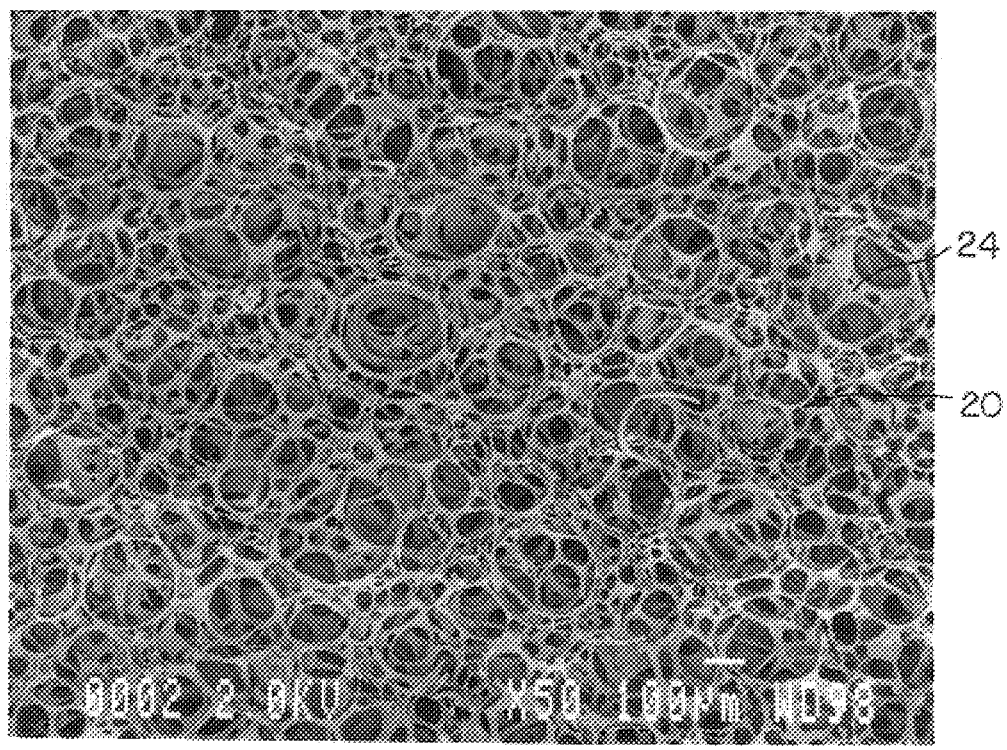
FIG. 4 is an SEM photograph of a surface of a two layer foam produced in accordance with the present invention.
Figure 5:
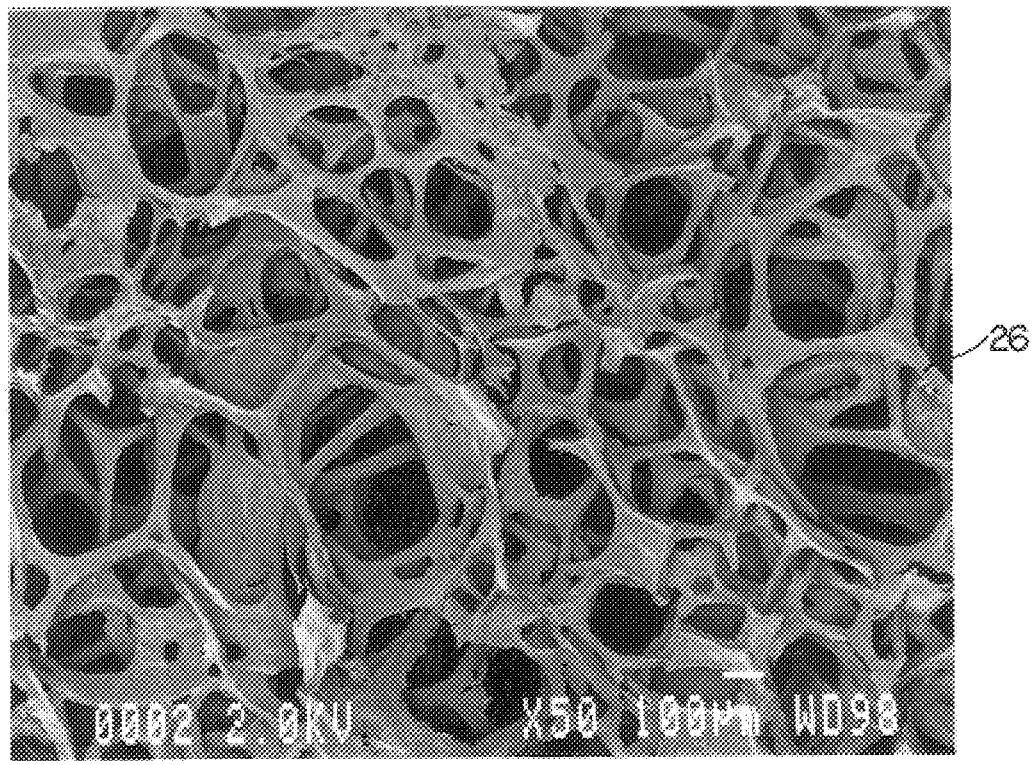
FIG. 5 is an SEM photograph of another surface of the two layer foam of FIG. 4.
Figure 6:
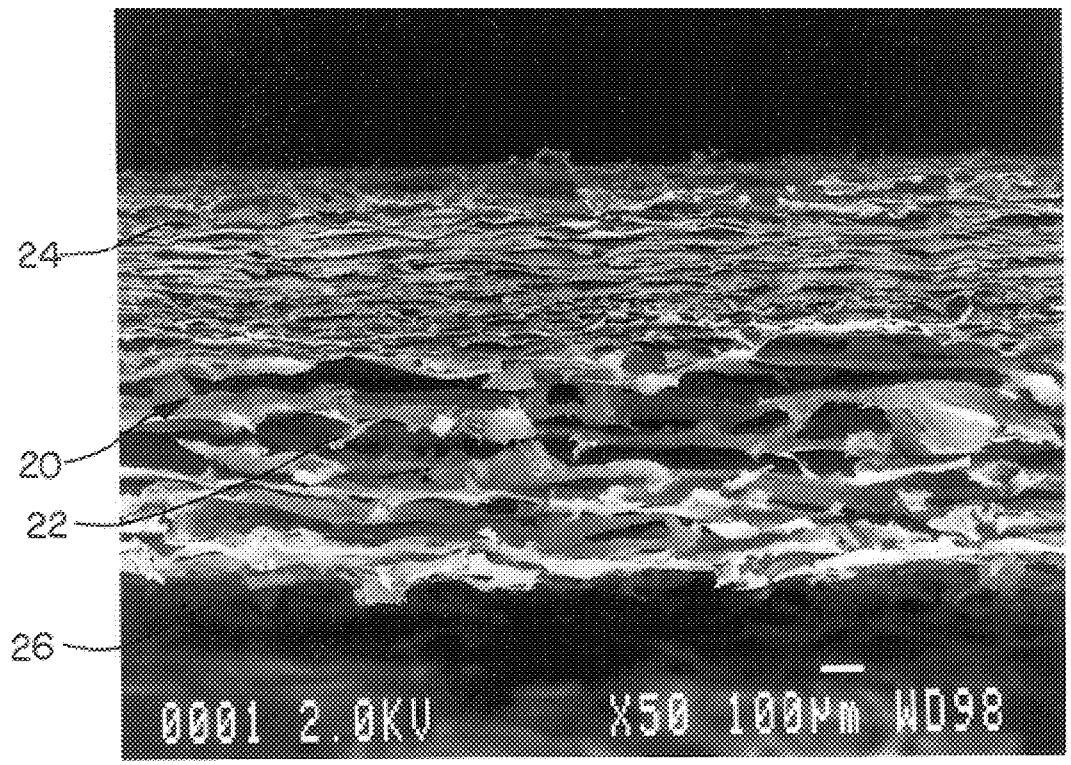
FIG. 6 is an SEM photogoraph of a cross section through the thickness of the two layer foam of FIGS. 4 and 5.

Another alginate foam layer was made by a method similar to the method of Example 4 above; this foam layer was foamed mechanically in accordance with the invention to have a relatively large mean pore size and dried. A second foam layer controlled to have a relatively smaller mean pore size was then cast on one surface of the first mentioned layer and dried. FIGS. 4 to 6 are Scanning Electron Microscope photographs of the resultant two-layer foam (20). It will be noted that an interior (22) of the foam is "collapsed", while the surfaces (24, 26) substantially maintain their controlled pore sizes and pore size distributions.

EXAMPLE 8

An aqueous solution containing 5 wt % sodium hyaluronate was prepared. To this solution was added 2.7 grams of sodium dodecyl sulphate and 5.3 grams of ammonium stearate per 100 grams of solution. The mixture was well beaten with a KitchenAid mixer to form a foam. The foam was spread onto a polyester sheet and air dried. Inspection under an optical microscope revealed the foam was an open-cell structure with fairly uniform pore size.

EXAMPLE 9

A solution was prepared with 10 grams of 37.5 w/w HCl and 490 grams water. Fifteen grams of chitosan were added and dissolved in the acid. To the solution were added 1.5 grams of sodium dodecyl sulfate and 15 grams of ammonium stearate. The mixture was beaten in a KitchenAid mixer to form a foam which was subsequently drawn to 25 mils thickness and air dried. Inspection under an optical microscope revealed the foam was open-celled and fairly uniform in pore size.

We claim:

1. A method of forming a dry polysaccharide foam from an aqueous polysaccharide solution comprised of the steps of:

a) forming an aqueous solution of a polysaccharide selected from the group consisting of alginic acid, a soluble alginate salt, and other soluble polysaccharides containing exchangeable counter-cations;

b) introducing a gas into the aqueous solution to form a wet foam by agitating the solution;

c) homogeneously dispersing an insoluble carbonate or hydrogen carbonate salt having one or more di- or tri-valent cations in the wet foam and subsequently treating the wet foam with an acid having a concentration not in excess of 1N thereby liberating carbon dioxide as a gas and the cations to produce a cross-linked polysaccharide foam; and d) drying the wet foam to form a dry polysaccharide foam;
   wherein the dry foam is predominantly comprised of polysaccharide.

2. The method as set forth in claim 1 wherein agitating the solution is effected by beating or by mechanical agitation.

3. The method as set forth in claim 1 wherein the polysaccharide is selected from the group consisting of a water soluble polysaccharide salt, a water soluble alginate, a water soluble hyaluronate, hyaluronic acid, carrageenans, guar gum, and carboxymethyl cellulose.

4. The method as set forth in claim 1 wherein the aqueous solution of polysaccharide contains at least one agent selected from the group consisting of foam stabilizers and foaming agents.

5. The method as set forth in claim 1 wherein the aqueous solution includes a foaming agent selected from the group consisting of sodium stearate, sodium dodecyl sulfate, alpha olefin sulfonates, sulfoalkyl amide, mono carboxyl coco imidazoline compounds, dicarboxyl coco imidazoline compounds, sulfated fatty polyoxyethylene quaternary nitrogen compounds, octylphenol ethoxylate, linear aliphatic polyethers and sorbitan esters.

6. The method as set forth in claim 1 further comprised of introducing a plasticizer in the aqueous solution selected from the group consisting of glycerol, glucose, polyhydric alcohols, triethanolamine and stearates.

7. The method as set forth in claim 1 further comprised of introducing an oligomeric or polymeric foam modifier in the aqueous solution selected from the group consisting of polyethylene glycol, guar gum, albumin, gelatin, carboxymethyl cellulose, hydroxyethyl cellulose, hydroxypropyl cellulose, polyacrylamide, polyacrylic acid, polyvinyl alcohol, polyvinyl pyrrolidone, polyoxazoline and polyethyeneimine.

8. The method as set forth in claim 7 wherein polyethylene glycol functionalized with vinyl groups is introduced as the foam modifier and the foam is irradiated to effect polymerization of the functionalized polyethylene glycol forming a polymer network in the foam.

9. A method as set forth in claim 1 further comprised of introducing a foam stabilizer into the aqueous solution selected from the group consisting of ammonium stearate, dodecyl alcohol, tetradecanol, hexadecanol, tridecyloxypolyethanol and polyoxyethylated oleylamine.

10. The method as set forth in claim 1 wherein the cross-linked foam is converted by treating the foam with an aqueous treating solution which in addition to water consists of a component containing solubilizing mono-valent cations so that at least a portion of the cross-linking di- or tri-valent cations in the foam are replaced by the mono-valent cations thereby imparting a degree of solubility to the foam in aqueous environments.

11. The method as set forth in claim 10 wherein the converted and cross-linked foam is washed and then redried.

12. A wound dressing, cell culture replicating medium, barrier medium or delivery device consisting essentially of polysaccharide foam produced in accordance with the method of claim 11.

13. The method as set forth in claim 1 wherein the dry polysaccharide foam foam is washed and then redried.

14. The method as set forth in claim 1 further comprised of washing and drying the cross-linked or coagulated wet foam to form a dry polysaccharide foam.

15. A wound dressing, cell culture replicating medium, barrier medium or delivery device consisting essentially of polysaccharide foam produced in accordance with the method of claim 14.

16. The method as set forth in claim 3 wherein the cross-linked wet foam is converted by treating the foam with an aqueous solution containing solubilizing mono-valent cations so that at least one of the cross-linking di- or tri-valent cations in the foam are replaced by the mono-valent cations thereby imparting a degree of solubility to the wet foam.

17. The method as set forth in claim 16 further comprises of washing and drying the converted and cross-linked wet foam to form a dry polysaccharide foam.

18. The method as set forth in claim 1 wherein at least one ingredient selected from the group consisting of particulate fillers, barium sulfate, fibres of cellulose or other fibrous materials, moisture retaining materials, and reinforcing filler materials are introduced into the aqueous solution.

19. The method as set forth in claim 1 wherein the wet foam is cast as a layer and dried to form a dry sheet of polysaccharide foam.

20. The method as set forth in claim 1 wherein the wet foam is cast in the form of buttons, beads, balls, cylinders or hemispheres or in the shape of a part of a human body or animal body and dried.

21. The method as set forth in claim 1 wherein the wet foam is cast as a layer on a substrate and dried.

22. The method as set forth in claim 21 wherein the substrate is a woven, non-woven fibrous article, a film, or a foam.

23. The method as set forth in claim 22 wherein the substrate is a layer of polysaccharide foam having a different mean pore size or pore size distribution relative to the cast foam layer.

24. A wound dressing, cell culture replicating medium, barrier medium or delivery device consisting essentially of polysaccharide foam produced in accordance with the method of claim 1.

* * * * *